(12) United States Patent
Lee et al.

(10) Patent No.: US 7,288,393 B2
(45) Date of Patent: Oct. 30, 2007

(54) NUCLEOTIDE SEQUENCE OF THREONINE OPERON IRREPRESSIBLE BY ISOLEUCINE AND METHOD FOR PRODUCING L-THREONINE USING TRANSFORMED HOST CELL CONTAINING THE SAME

(75) Inventors: Hee Jong Lee, Anyang (KR); Seong Jun Kim, Suwon (KR); Jin Suck Sung, Yongin (KR); Seok Won Song, Goyang (KR); Young Hoon Park, Seongnam (KR)

(73) Assignee: CJ Corporation (KR)

( * ) Notice: Subject to any disclaimer, the term of this patent is extended or adjusted under 35 U.S.C. 154(b) by 363 days.

(21) Appl. No.: 10/514,348

(22) PCT Filed: May 15, 2003

(86) PCT No.: PCT/KR03/00955

§ 371 (c)(1),
(2), (4) Date: Nov. 12, 2004

(87) PCT Pub. No.: WO03/097839

PCT Pub. Date: Nov. 27, 2003

(65) Prior Publication Data

US 2005/0221449 A1    Oct. 6, 2005

(30) Foreign Application Priority Data

May 15, 2002   (KR) .................. 10-2002-0026725

(51) Int. Cl.
*C12P 13/08*   (2006.01)
*C12N 1/21*    (2006.01)
*C12N 9/00*    (2006.01)
*C12N 9/02*    (2006.01)
*C12N 9/12*    (2006.01)
*C12N 15/63*   (2006.01)
*C07H 21/04*   (2006.01)

(52) U.S. Cl. .............. 435/115; 435/252.3; 435/252.32; 435/252.33; 435/320.1; 536/23.1; 536/23.2; 536/23.7

(58) Field of Classification Search ............... None
See application file for complete search history.

(56) References Cited

OTHER PUBLICATIONS

Park et al. (Nov. 2002) Biotechnology Letters, vol. 24, pp. 1815-1819.*
Lynn et al. (Jan. 5, 1988) J. Biol. Chem., vol. 263, No. 1, pp. 472-479.*
Noh et al. (1991) Misaengmul Hakhoechi, vol. 29, No.3, pp. 149-154.*
Jeng et al (1990) JBC, vol. 265, No. 7, pp. 3823-3830.*
Katinka et al. (1980) PNAS, vol. 77, No. 10, pp. 5730-5733.*

* cited by examiner

*Primary Examiner*—Elizabeth Slobodyansky
(74) *Attorney, Agent, or Firm*—Cantor Colburn LLP

(57) ABSTRACT

A nucleotide sequence of the threonine operon of *E. coli* with a deletion of all or part of a nucleotide fragment of −56 to −18, a recombinant vector containing the above nucleotide sequence, and a transformed host cell containing the recombinant vector are provided. A method for producing L-threonine comprising culturing the transformed host cell is also provided.

8 Claims, No Drawings

SEQUENCE LISTING

```
<160> NUMBER OF SEQ ID NOS: 4

<210> SEQ ID NO 1
<211> LENGTH: 5020
<212> TYPE: DNA
<213> ORGANISM: Esherichia coli

<400> SEQUENCE: 1
agcttttcat tctgactgca acgggcaata tgtctctgtg tggattaaaa aaagagtgtc      60
tgatagcagc ttctgaactg gttacctgcc gtgagtaaat taaaatttta ttgacttagg     120
tcactaaata ctttaaccaa tataggcata gcgcacagac agataaaaat tacagagtac     180
acaacatcca tgaaacgcat tagcaccacc attaccacca ccatcaccat taccacaggt     240
aacggtgcgg gctgacgcgt acaggaaaca cagaaaaaag cccgcacctg acagtgcggg     300
cttttttttt cgaccaaagg taacgaggta acaaccatgc gagtgttgaa gttcggcggt     360
acatcagtgg caaatgcaga acgttttctg cgtgttgccg atattctgga aagcaatgcc     420
aggcaggggc aggtggccac cgtcctctct gcccccgcca aaatcaccaa ccacctggtg     480
gcgatgattg aaaaaaccat tagcggccag gatgctttac ccaatatcag cgatgccgaa     540
cgtatttttg ccgaactttt gacgggactc gccgccgccc agccgggtt cccgctggcg      600 caattgaaaa ctttcgtcga tcaggaattt gcccaaataa aacatgtcct gcatggcatt     660
agtttgttgg ggcagtgccc ggatagcatc aacgctgcgc tgatttgccg tggcgagaaa     720
atgtcgatcg ccattatggc cggcgtatta gaagcgcgcg gtcacaacgt tactgttatc     780
gatccggtcg aaaaactgct ggcagtgggg cattacctcg aatctaccgt cgatattgct     840
gagtccaccc gccgtattgc ggcaagccgc attccggctg atcacatggt gctgatggca     900
ggtttcaccg ccgtaatga aaaaggcgaa ctggtggtgc ttggacgcaa cggttccgac     960
tactctgctg cggtgctggc tgcctgttta cgcgccgatt gttgcgagat tggacggac    1020
```

-continued

```
gttgacgggg tctatacctg cgacccgcgt caggtgcccg atgcgaggtt gttgaagtcg    1080
atgtcctacc aggaagcgat ggagctttcc tacttcggcg ctaaagttct tcaccccgc     1140 accattaccc ccatcgccca gttccagatc ccttgcctga ttaaaaatac cggaaatcct    1200
caagcaccag gtacgctcat tggtgccagc cgtgatgaag acgaattacc ggtcaagggc    1260
atttccaatc tgaataacat ggcaatgttc agcgtttctg gtccggggat gaaagggatg    1320
gtcggcatgg cggcgcgcgt cttttgcagcg atgtcacgcg cccgtatttc cgtggtgctg    1380
attacgcaat catcttccga atacagcatc agtttctgcg ttccacaaag cgactgtgtg    1440
cgagctgaac gggcaatgca ggaagagttc tacctggaac tgaaagaagg cttactggag    1500
ccgctggcag tgacggaacg gctggccatt atctcggtgg taggtgatgg tatgcgcacc    1560
ttgcgtggga tctcggcgaa attctttgcc gcactggccc gcgccaatat caacattgtc    1620
gccattgctc aggatcttc tgaacgctca atctctgtcg tggtaaataa cgatgatgcg    1680
accactggcg tgcgcgttac tcatcagatg ctgttcaata ccgatcaggt tatcgaagtg    1740
tttgtgattg gcgtcggtgg cgttggcggt gcgctgctgg agcaactgaa gcgtcagcaa    1800
agctggctga agaataaaca tatcgactta cgtgtctgcg gtgttgccaa ctcgaaggct    1860
ctgctcacca atgtacatgg ccttaatctg gaaaactggc aggaagaact ggcgcaagcc    1920
aaagagccgt taatctcgg gcgcttaatt cgcctcgtga agaatatca tctgctgaac    1980 ccggtcattg ttgactgcac ttccagccag gcagtggcgg atcaatatgc cgacttcctg    2040
cgcgaaggtt ccacgttgt cacgccgaac aaaaaggcca cacctcgtc gatggattac    2100 taccatcagt tgcgttatgc ggcgaaaaaa tcgcggcgta aattcctcta tgacaccaac    2160 gttgggctg gattaccggt tattgagaac ctgcaaaatc tgctcaatgc aggtgatgaa    2220
ttgatgaagt ctccggcat tcttttctggt tcgctttctt atatcttcgg caagttagac    2280
gaaggcatga gtttctccga ggcgaccacg ctggcgcggg aaatgggtta taccgaaccg    2340
gacccgcgag atgatctttc tggtatggat gtggcgcgta aactattgat tctcgctcgt    2400
gaaacgggac gtgaactgga gctggcggat attgaaattg aacctgtgct gcccgcagag    2460
tttaacgccg agggtgatgt tgccgctttt atggcgaatc tgtcacaact cgacgatctc    2520
tttgccgcgc gcgtggcgaa ggcccgtgat gaaggaaaag ttttgcgcta tgttggcaat    2580
attgatgaag atggcgtctg ccgcgtgaag attgccgaag tggatggtaa tgatccgctg    2640
ttcaaagtga aaaatggcga aaacgccctg gccttctata gccactatta tcagccgctg    2700
ccgttggtac tgcgcggata tggtgcgggc aatgacgtta cagctgccgg tgtcttggct    2760
gatctgctac gtaccctctc atggaagtta ggagtctgac atggttaaag tttatgcccc    2820
ggcttccagt gccaatatga gcgtcgggtt tgatgtgctc ggggcggcgg tgacacctgt    2880
tgatggtgca ttgctcggag atgtagtcac ggttgaggcg gcagagacat tcagtctcaa    2940
caacctcgga cgctttgccg ataagctgcc gtcagaacca cgggaaaata tcgtttatca    3000
gtgctgggag cgttttttgcc aggaactggg taagcaaatt ccagtggcga tgaccctgga    3060
aaagaatatg ccgatcggtt cgggcttagg ctccagtgcc tgttcggtgg tcgcggcgct    3120
gatggcgatg aatgaacact gcggcaagcc gcttaatgac actcgtttgc tggctttgat    3180
gggcgagctg gaaggccgta tctccggcag cattcattac gacaacgtgg caccgtgttt    3240
tctcggtggt atgcagttga tgatcgaaga aaacgacatc atcagccagc aagtgccagg    3300
gtttgatgag tggctgtggg tgctggcgta tccggggatt aaagtctcga cggcagaagc    3360
```

-continued

```
cagggctatt ttaccggcgc agtatcgccg ccaggattgc attgcgcacg ggcgacatct    3420
ggcaggcttc attcacgcct gctattcccg tcagcctgag cttgccgcga agctgatgaa    3480
agatgttatc gctgaaccct accgtgaacg gttactgcca ggcttccggc aggcgcggca    3540
ggcggtcgcg gaaatcggcg cggtagcgag cggtatctcc ggctccggcc cgaccttgtt    3600
cgctctgtgt gacaagccgg aaaccgccca gcgcgttgcc gactggttgg gtaagaacta    3660
cctgcaaaat caggaaggtt tgttcatat ttgccggctg gatacggcgg gcgcacgagt     3720
actggaaaac taaatgaaac tctacaatct gaaagatcac aacgagcagg tcagctttgc    3780
gcaagccgta acccagggt tgggcaaaaa tcaggggctg ttttttccgc acgacctgcc     3840
ggaattcagc ctgactgaaa ttgatgagat gctgaagctg gattttgtca cccgcagtgc    3900
gaagatcctc tcggcgttta ttggtgatga atcccacag gaaatcctgg aagagcgcgt     3960
gcgcgcggcg tttgccttcc cggctccggt cgccaatgtt gaaagcgatg tcggttgtct    4020
ggaattgttc cacgggccaa cgctggcatt taaagatttc ggcggtcgct ttatggcaca    4080
aatgctgacc catattgcgg gtgataagcc agtgaccatt ctgaccgcga cctccggtga    4140
taccggagcg gcagtggctc atgctttcta cggtttaccg aatgtgaaag tggttatcct    4200
ctatccacga ggcaaaatca gtccactgca agaaaaactg ttctgtacat gggcggcaa    4260
tatcgaaact gttgccatcg acggcgattt cgatgcctgt caggcgctgg tgaagcaggc    4320
gtttgatgat gaagaactga agtggcgct agggttaaac tcggctaact cgattaacat    4380
cagccgtttg ctggcgcaga tttgctacta ctttgaagct gttgcgcagc tgccgcagga    4440
gacgcgcaac cagctggttg tctcggtgcc aagcggaaac ttcggcgatt tgacggcggg    4500
tctgctggcg aagtcactcg gtctgccggt gaaacgtttt attgctgcga ccaacgtgaa    4560
cgataccgtg ccacgtttcc tgcacgacgg tcagtggtca cccaaagcga ctcaggcgac    4620
gttatccaac gcgatggacg tgagtcagcc gaacaactgg ccgcgtgtgg aagagttgtt    4680
ccgccgcaaa atctggcaac tgaaagagct gggttatgca gccgtggatg atgaaaccac    4740
gcaacagaca atgcgtgagt aaaagaact gggctacact tcggagccgc acgctgccgt     4800
agcttatcgt gcgctgcgtg atcagttgaa tccaggcgaa tatggcttgt tcctcggcac    4860
cgcgcatccg gcgaaattta agagagcgt ggaagcgatt ctcggtgaaa cgttggatct     4920
gccaaaagag ctggcagaac gtgctgattt acccttgctt tcacataatc tgcccgccga    4980
ttttgctgcg ttgcgtaaat tgatgatgaa tcatcagtaa                          5020
```

```
<210> SEQ ID NO 2
<211> LENGTH: 4981
<212> TYPE: DNA
<213> ORGANISM: Artificial Sequence
<220> FEATURE:
<223> OTHER INFORMATION: mutated sequence of threonine operon

<400> SEQUENCE: 2
```

```
agcttttcat tctgactgca acgggcaata tgtctctgtg tggattaaaa aaagagtgtc      60
tgatagcagc ttctgaactg gttacctgcc gtgagtaaat taaaatttta ttgacttagg    120
tcactaaata ctttaaccaa tataggcata gcgcacagac agataaaaat tacagagtac    180
acaacatcca tgaaacgcat tagcaccacc attaccacca ccatcaccat taccacaggt    240
aacggtgcgg gctgacgcgt acaggaaaca cagaaaaaag gtaacgaggt aacaaccatg    300
cgagtgttga agttcggcgg tacatcagtg gcaaatgcag aacgttttct gcgtgttgcc    360
gatattctgg aaagcaatgc caggcagggg caggtggcca ccgtcctctc tgcccccgcc    420
```

-continued

| | |
|---|---|
| aaaatcacca accacctggt ggcgatgatt gaaaaaacca ttagcggcca ggatgcttta | 480 |
| cccaatatca gcgatgccga acgtattttt gccgaacttt tgacgggact cgccgccgcc | 540 |
| cagccgggt tcccgctggc gcaattgaaa actttcgtcg atcaggaatt tgcccaaata | 600 |
| aaacatgtcc tgcatggcat tagtttgttg gggcagtgcc cggatagcat caacgctgcg | 660 |
| ctgatttgcc gtggcgagaa aatgtcgatc gccattatgg ccggcgtatt agaagcgcgc | 720 |
| ggtcacaacg ttactgttat cgatccggtc gaaaaactgc tggcagtggg gcattacctc | 780 |
| gaatctaccg tcgatattgc tgagtccacc cgccgtattg cggcaagccg cattccggct | 840 |
| gatcacatgg tgctgatggc aggtttcacc gccggtaatg aaaaaggcga actggtggtg | 900 |
| cttggacgca acggttccga ctactctgct gcggtgctgg ctgcctgttt acgcgccgat | 960 |
| tgttgcgaga tttggacgga cgttgacggg gtctatacct gcgacccgcg tcaggtgccc | 1020 |
| gatgcgaggt tgttgaagtc gatgtcctac caggaagcga tggagctttc ctacttcggc | 1080 |
| gctaaagttc ttcacccccg caccattacc cccatcgccc agttccagat cccttgcctg | 1140 |
| attaaaaata ccggaaatcc tcaagcacca ggtacgctca ttggtgccag ccgtgatgaa | 1200 |
| gacgaattac cggtcaaggg catttccaat ctgaataaca tggcaatgtt cagcgtttct | 1260 |
| ggtccgggga tgaaagggat ggtcggcatg gcggcgcgcg tctttgcagc gatgtcacgc | 1320 |
| gcccgtattt ccgtggtgct gattacgcaa tcatcttccg aatacagcat cagtttctgc | 1380 |
| gttccacaaa gcgactgtgt gcagctgaac cgggcaatgc aggaagagtt ctacctggaa | 1440 |
| ctgaaagaag gcttactgga gccgctggca gtgacgaaac ggctggccat tatctcggtg | 1500 |
| gtaggtgatg gtatgcgcac cttgcgtggg atctcggcga aattctttgc cgcactggcc | 1560 |
| cgcgccaata tcaacattgt cgccattgct cagggatctt ctgaacgctc aatctctgtc | 1620 |
| gtggtaaata cgatgatgc gaccactggc gtgcgcgtta ctcatcagat gctgttcaat | 1680 |
| accgatcagg ttatcgaagt gtttgtgatt ggcgtcggtg gcgttggcgg tgcgctgctg | 1740 |
| gagcaactga gcgtcagca agctggctg aagaataaac atatcgactt acgtgtctgc | 1800 |
| ggtgttgcca actcgaaggc tctgctcacc aatgtacatg gccttaatct ggaaaactgg | 1860 |
| caggaagaac tggcgcaagc caaagagccg tttaatctcg ggcgcttaat tcgcctcgtg | 1920 |
| aaagaatatc atctgctgaa cccggtcatt gttgactgca cttccagcca ggcagtggcg | 1980 |
| gatcaatatg ccgacttcct gcgcgaaggt ttccacgttg tcacgccgaa caaaaaggcc | 2040 |
| aacacctcgt cgatggatta ctaccatcag ttgcgttatg cggcgaaaa atcgcggcgt | 2100 |
| aaattcctct atgacaccaa cgttggggct ggattaccgg ttattgagaa cctgcaaaat | 2160 |
| ctgctcaatg caggtgatga attgatgaag ttctccggca ttctttctgg ttcgcttttct | 2220 |
| tatatcttcg gcaagttaga cgaaggcatg agtttctccg aggcgaccac gctggcgcgg | 2280 |
| gaaatgggtt ataccgaacc ggaccccgga gatgatcttt ctggtatgga tgtgcgcgt | 2340 |
| aaactattga ttctcgctcg tgaaacggga cgtgaactgg agctggcgga tattgaaatt | 2400 |
| gaacctgtgc tgcccgcaga gtttaacgcc gagggtgatg ttgccgcttt tatggcgaat | 2460 |
| ctgtcacaac tcgacgatct cttttgccgcg cgcgtggcga aggcccgtga tgaaggaaaa | 2520 |
| gttttgcgct atgttggcaa tattgatgaa gatggcgtct gccgcgtgaa gattgccgaa | 2580 |
| gtggatggta atgatccgct gttcaaagtg aaaaatggcg aaaacgccct ggccttctat | 2640 |
| agccactatt atcagccgct gccgttggta ctgcgcggat atggtgcggg caatgacgtt | 2700 |
| acagctgccg gtgtctttgc tgatctgcta cgtacccttct catggaagtt aggagtctga | 2760 |

| | |
|---|---|
| catggttaaa gtttatgccc cggcttccag tgccaatatg agcgtcgggt ttgatgtgct | 2820 |
| cggggcggcg gtgacacctg ttgatggtgc attgctcgga gatgtagtca cggttgaggc | 2880 |
| ggcagagaca ttcagtctca acaacctcgg acgctttgcc gataagctgc cgtcagaacc | 2940 |
| acgggaaaat atcgtttatc agtgctggga gcgttttgc caggaactgg gtaagcaaat | 3000 |
| tccagtggcg atgaccctgg aaaagaatat gccgatcggt tcgggcttag gctccagtgc | 3060 |
| ctgttcggtg gtcgcggcgc tgatggcgat gaatgaacac tgcggcaagc cgcttaatga | 3120 |
| cactcgtttg ctggctttga tgggcgagct ggaaggccgt atctccggca gcattcatta | 3180 |
| cgacaacgtg gcaccgtgtt ttctcggtgg tatgcagttg atgatcgaag aaaacgacat | 3240 |
| catcagccag caagtgccag ggtttgatga gtggctgtgg gtgctggcgt atccggggat | 3300 |
| taaagtctcg acggcagaag ccagggctat tttaccggcg cagtatcgcc gccaggattg | 3360 |
| cattgcgcac gggcgacatc tggcaggctt cattcacgcc tgctattccc gtcagcctga | 3420 |
| gcttgccgcg aagctgatga agatgttat cgctgaaccc taccgtgaac ggttactgcc | 3480 |
| aggcttccgg caggcgcggc aggcggtcgc ggaaatcggc gcggtagcga gcggtatctc | 3540 |
| cggctccggc ccgaccttgt tcgctctgtg tgacaagccg gaaaccgccc agcgcgttgc | 3600 |
| cgactggttg ggtaagaact acctgcaaaa tcaggaaggt tttgttcata tttgccggct | 3660 |
| ggatacggcg ggcgcacgag tactggaaaa ctaaatgaaa ctctacaatc tgaaagatca | 3720 |
| caacgagcag gtcagctttg cgcaagccgt aacccagggg ttgggcaaaa atcagggct | 3780 |
| gttttttccg cacgacctgc cggaattcag cctgactgaa attgatgaga tgctgaagct | 3840 |
| ggattttgtc acccgcagtg cgaagatcct ctcggcgttt attggtgatg aaatcccaca | 3900 |
| ggaaatcctg gaagagcgcg tgcgcgcggc gtttgccttc ccggctccgg tcgccaatgt | 3960 |
| tgaaagcgat gtcggttgtc tggaattgtt ccacgggcca acgctggcat ttaaagattt | 4020 |
| cggcggtcgc tttatggcac aaatgctgac ccatattgcg ggtgataagc cagtgaccat | 4080 |
| tctgaccgcg acctccggtg ataccggagc ggcagtggct catgctttct acggtttacc | 4140 |
| gaatgtgaaa gtggttatcc tctatccacg aggcaaaatc agtccactgc aagaaaaact | 4200 |
| gttctgtaca ttgggcggca atatcgaaac tgttgccatc gacggcgatt tcgatgcctg | 4260 |
| tcaggcgctg gtgaagcagg cgtttgatga tgaagaactg aaagtggcgc tagggttaaa | 4320 |
| ctcggctaac tcgattaaca tcagccgttt gctggcgcag atttgctact actttgaagc | 4380 |
| tgttgcgcag ctgccgcagg agacgcgcaa ccagctggtt gtctcggtgc caagcggaaa | 4440 |
| cttcggcgat ttgacggcgg gtctgctggc gaagtcactc ggtctgccgg tgaaacgttt | 4500 |
| tattgctgcg accaacgtga acgataccgt gccacgtttc ctgcacgacg gtcagtggtc | 4560 |
| acccaaagcg actcaggcga cgttatccaa cgcgatggac gtgagtcagc cgaacaactg | 4620 |
| gccgcgtgtg gaagagttgt tccgccgcaa aatctggcaa ctgaaagagc tgggttatgc | 4680 |
| agccgtggat gatgaaacca cgcaacagac aatgcgtgag ttaaaagaac tgggctacac | 4740 |
| ttcggagccg cacgctgccg tagcttatcg tgcgctgcgt gatcagttga atccaggcga | 4800 |
| atatggcttg ttcctcggca ccgcgcatcc ggcgaaattt aaagagagcg tggaagcgat | 4860 |
| tctcggtgaa acgttggatc tgccaaaaga gctggcagaa cgtgctgatt tacccttgct | 4920 |
| ttcacataat ctgcccgccg attttgctgc gttgcgtaaa ttgatgatga atcatcagta | 4980 |
| a | 4981 |

```
<210> SEQ ID NO 3
<211> LENGTH: 23
```

```
<212> TYPE: DNA
<213> ORGANISM: Artificial Sequence
<220> FEATURE:
<223> OTHER INFORMATION: Thr-F primer sequence

<400> SEQUENCE: 3
ctggtcgact ggttacaaca acg                                              23

<210> SEQ ID NO 4
<211> LENGTH: 23
<212> TYPE: DNA
<213> ORGANISM: Artificial Sequence
<220> FEATURE:
<223> OTHER INFORMATION: Thr-R primer sequence

<400> SEQUENCE: 4
ggactaacgt aatttccgca gcc                                              23
```

NUCLEOTIDE SEQUENCE OF THREONINE OPERON IRREPRESSIBLE BY ISOLEUCINE AND METHOD FOR PRODUCING L-THREONINE USING TRANSFORMED HOST CELL CONTAINING THE SAME

TECHNICAL FIELD

The present invention relates to a nucleotide sequence of the threonine operon of *Escherichia coli* with a deletion of all or part of a nucleotide fragment of −56 to −18, a recombinant vector containing the above nucleotide sequence, and a transformed host cell containing the recombinant vector. The present invention also provides a method for producing L-threonine comprising culturing the transformed host cell.

BACKGROUND ART

L-threonine is an essential amino acid and is widely used as a feed or food additive. In addition, L-threonine is used as a medical solution or a raw material for a drug synthesis.

L-threonine is produced by a fermentation process using a mutant strain derived from a wild-type strain of *Escherichia coli* (*E. coli*), *Corynebacteria* sp., *Serratia* sp., or *Providencia* sp. Examples of the mutant strain include an amino acid analogue- or drug-resistant mutant strain, or a variety of auxotroph to diaminopimeric acid, methionine, lysine, or isoleucine [Japanese Patent Laid-Open Publication No. Hei. 2-219582; *Appl. Microbiol. Biotechnol.*, 29. 550-553 (1988); Korean Patent No. 1992-8365].

A fermentation process using a recombinant strain can also be used to produce L-threonine. Japanese Patent Laid-Open Publication No. Hei. 5-10076 discloses a method for producing threonine in large scale using a recombinant strain of *Serratia* sp. containing a DNA fragment with genetic information of aspartokinase, homoserine kinase, homoserine dehydrogenase, and threonine synthase. In addition, a method for mass-producing L-threonine using a gene derived from a strain of *Providencia* sp. resistant to antagonist of methionine metabolism is disclosed in Japanese Patent Laid-Open Publication No. Hei. 1-289493.

As a method for producing threonine by regulation of expression of threonine operon, replacing a promoter of the threonine operon with tac promoter (WO 98/04715) and replacing an expression regulatory region of the threonine operon with cl repressor and PR promoter of *E. coli* λ phage (EP 0593792B1) are disclosed.

The threonine biosynthesis operon of *E. coli* is composed of genes, thrA, thrB, and thrC. The thrA gene encodes for aspartokinase and homoserine dehydrogenase, the thrB gene encodes for homoserine kinase, and the thrC gene encodes for threonine synthase. A leader sequence and attenuator of these genes precedes the threonine operon [*Proc. Natl. Acad. Sci. America* (1979), 76: 1706-1710]. One example of the nucleotide sequence of the threonine operon comprising the leader sequence, the attenuator, and the structural thr genes is as set forth in SEQ ID NO: 1. The ATG codon of nucleotide positions 337-339 of SEQ ID NO: 1 is a start codon for the threonine operon. In particular, the expression of the threonine operon is regulated by the intracellular levels of both threonine and isoleucine. This is similar to the regulatory mechanism of the tryptophan operon [*J. Bacteriology* (1975), 161-166].

DISCLOSURE OF THE INVENTION

For the threonine-producing strain that is not repressed by threonine or isoleucine, the present inventors have achieved the goals of the present invention by providing the mutant threonine operon which contains a defective attenuator region.

Therefore, the present invention is to provide a nucleotide sequence of the threonine operon that is not repressible by isoleucine.

The present invention is also to provide a recombinant vector containing the above nucleotide sequence of the threonine operon.

The present invention is also to provide a transformed host cell containing the recombinant vector.

The present invention is further to provide a method for producing L-threonine comprising culturing the transformed host cell.

According to an aspect of the present invention, there is provided a nucleotide sequence of the threonine operon of *E. coli* with a deletion of all or part of a 39 bp nucleotide fragment of −56 to −18 that is attenuator of the structural genes of the threonine operon. In this case, the nucleotide sequences in an upstream region from the A of the start codon, ATG (+1) are numbered as negative numbers, and the nucleotide sequences in a downstream region as positive numbers. Unless specified otherwise, the nucleotide numbering is as defined in the above.

According to another aspect of the present invention, there is provided a recombinant vector containing the above nucleotide sequence of the threonine operon of *E. coli*. The recombinant vector can be manufactured by a conventional method comprising digesting the threonine operon of *E. coli* and a suitable vector with restriction enzymes such as ApaI and PstI, followed by ligation. The suitable vector may be phage, plasmid, and cosmid, for examples. Examples of the phage and cosmid vectors include pWE15, M13, λEMBL3, λEMBL4, λFIXII, λDASHII, λZAPII, λgt10, λgt11, Charon4A, and Charon21A.

Examples of the plasmid vector include pBR series, pUC series, pBluescriptII series, pGEM series, pTZ series, and pET series. In addition, various shuttle vectors that can replicate in a variety of host cells such as *E. coli* and *Corynebacteria* may be used. Preferably, pECCG122 (KFCC 10696), which has been deposited the Korean Federation of Culture Collection (KFCC) on Jun. 20, 1990, is used as the cloning vector.

According to another aspect of the present invention, there is provided a novel microorganism containing the above recombinant vector. The microorganism may be manufactured by transforming a host cell with the recombinant vector using a conventional method [Sambrook, J. et al., 2th (1989), Cold Spring Harbor Laboratory Press].

A host cell may be gram-negative bacteria. Cells belong to the genus *Escherichia* sp. are most preferred. In particular, according to the preferred embodiment of the present invention, *E. coli* KCCM 10236 (Korean Patent Application No. 2001-6976) is used as a host cell. The *E. coli* KCCM 10236 is an auxotroph for methionine and is resistant to threonine analogue (AHV: α-amino-β-hydroxyvaleric acid), lysine analogue (AEC: S-(2-aminoethyl)-L-cysteine), isoleucine analogue (α-aminobutyric acid), and methionine analogue (ethionine). In addition, the *E. coli* KCCM 10236 has an extra copy of phosphoenol pyruvate carboxylase gene in a chromosomal DNA and at least one of the thrA, thrB, and thrC genes is present in an amplified state, thereby its productivity of L-threonine is increased. In the present invention, the effects of the above recombinant vector were confirmed by using *Escherichia coli* KFCC 10236 as a host cell. The *Escherichia coli* KFCC 10236 has been deposited in the Korean Federation of Culture Collection (KFCC) on Dec. 29, 2000.

According to yet another aspect of the present invention, there is provided a method for producing L-threonine comprising culturing the transformed host cell and recovering L-threonine from the culture. Preferably, *E. coli* KCCM 10236/pTHR(+) is used as the transformed host cell.

The method for producing L-threonine of the present invention may be carried out under a conventional condition. Although the intracellular levels of isoleucine and threonine are high, the production of L-threonine is not inhibited. Thereby the productivity of L-threonine is increased.

Hereinafter, the present invention will be described more specifically by examples. However, the following examples are provided only for illustrations and thus the present invention is not limited to or by them.

EXAMPLES

Example 1 showed correlation between isoleucine concentration in a culture medium and L-threonine biosynthesis using a conventional L-threonine-producing strain. The nucleotide sequence of the threonine operon (hereinafter, simply referred to as "the thr operon") was cloned from the strain of Example 1 (Example 2). Then, mutation was induced on the pTHR (−) vector containing the cloned thr operon (Example 3) and strains of which the expression of the thr operon cannot be repressed by isoleucine and threonine were selected (Example 4). Finally, in Example 5, the thr operon of the selected strains was sequenced. As a result, a part of the attenuator in the thr operon was deleted.

Example 1

Correlation Between Isoleucine Concentration in Culture Medium and L-threonine Biosynthesis

*E. coli* KCCM 10236 strains were fed-batch cultured in a fermenter with capacity of 30 liter for 77 hours while maintaining a culture temperature of 32° C., a culture pH of 6.5, and aeration rate of 0.5 to 1.0 vvm. The composition and concentration of amino acids in the final culture medium were determined by an automatic amino acid analyzer. The results are presented in Table 1.

TABLE 1

Composition and concentration of amino acids in *E. coli* KCCM 10236 culture medium

| Amino acid | Concentration (g/l) | Amino acid | Concentration (g/l) |
|---|---|---|---|
| Aspartate | 0.00 | Alanine | 0.10 |
| Glutamate | 1.20 | Tyrosine | 0.00 |
| Asparagine | 0.00 | Methionine | 0.38 |
| Serine | 0.07 | Valine | 0.73 |
| Glutamine | 0.00 | Phenylalanine | 0.33 |
| Histidine | 0.00 | Isoleucine | 0.67 |
| Glycine | 0.00 | Leucine | 0.59 |
| Threonine | 115.20 | Lycine | 0.00 |
| Arginine | 0.00 | | |

In order to investigate the productivity of L-threonine depending on the added amount of L-isoleucine, 0 to 0.4 g/l of L-isoleucine was added to fermentation media and the resultant media were incubated in a flask for 48 hours. The results are shown in Table 2.

TABLE 2

Effect of addition of L-isoleucine on productivity of L-threonine of *E. coli* KCCM 10236

| amount of L-isoleucine (g/l) | concentration of L-threonine (g/l) | Productivity of L-threonine (%) |
|---|---|---|
| 0 | 18.7 | 37.4 |
| 0.05 | 16.8 | 33.6 |
| 0.10 | 9.52 | 19.0 |
| 0.20 | 8.26 | 16.5 |
| 0.40 | 8.35 | 16.7 |

As shown in Table 2, in the case of a conventional threonine production strain, *E. coli* KCCM 10236, as increasing the amount of L-isoleucine, the productivity of L-threonine was rapidly reduced.

Example 2

Cloning of Nucleotide Sequence of thr Operon in *E. coli* KCCM 10236

The thr operon was amplified and cloned from *E. coli* KCCM 10236. Primers for amplification of the thr operon were thr-F and thr-R as set forth in SEQ ID NO: 3 and SEQ ID NO: 4, respectively. The primer sequences were designed using the GenBank database (NCBI).

5447 bp of the thr operon containing promoter region was amplified using Expand™ High Fidelity PCR System (Boehringer Mannheim). The PCR reaction mixture contained 200 μM of each dNTP, 300 nM of each primer, 0.1 μg of *E. coli* KCCM 10236 genomic DNA, 1× Expand HF buffer with 15 mM MgCl$_2$, and 2.6 U of Expand™ High Fidelity PCR System enzyme mix. The PCR reaction was performed at 95° C. for 5 minutes, 95° C. for 30 seconds, 56° C. for 30 seconds, and 68° C. for 4 minutes and 30 seconds for 30 cycles to amplify the thr operon. The PCR reaction was maintained at 68° C. for 10 minutes and then terminated at 4° C. The amplified thr operon was inserted into a cloning vector, pGEM-T (Promega, America). Then, *E. coli* DH5a was transformed with the cloning vector containing the thr operon to obtain a pGEM-Thr vector.

The pGEM-Thr and pECCG 122 (KFCC 10696) vectors were digested with restriction enzymes, ApaI and PstI, and ligated with the thr operon and pECCG122 vector using a conventional method. *E. coli* DH5a was transformed with the ligation product to obtain a pTHR(−) vector. According to sequencing analysis, the cloned thr operon contained the nucleotide sequence of a conventional thr operon as set forth in SEQ ID NO: 1.

Example 3

Mutation of THR(−)

In order to induce mutation on the thr operon, 2 μg of the pTHR(−) DNA containing the thr operon was dissolved in 200 μl of buffer (0.1M KH$_2$PO$_4$-1 mM EDTA, pH 6.0) containing 200-500 μg/ml of N-methyl-N'-nitro-N-nitrosoguanidine and incubated at 37° C. for 10-30 minutes. The mutation-induced vector was recovered using a conventional alcohol precipitation and *E. coli* W3110 (ATCC27325) was transformed with the recovered vector.

Then, the transformed *E. coli* W3110 culture was plated on a LB medium containing 50 mg/l of kanamycine to obtain colonies grown on the LB medium. The colonies were replica plated onto a selective minimal medium plate containing isoleucine hydroxamate as an isoleucine analogue and α-amino-β-hydroxyvaleric acid (AHV) as a threonine analogue and onto a control minimal medium plate without containing these analogues, Strains grown onto the selective minimal medium plate were selected. After the replica plating was repeated three times, 27 candidate strains were selected. Then, the selected candidate strains were again inoculated onto selective minimal media plate containing isoleucine hydroxamate as an isoleucine analogue and α-amino-β-hydroxyvaleric acid (AHV) as a threonine analogue to thereby reconfirm the growth of the candidate strains on the selective minimal media plate.

Example 4

Determination of Nucleotide Sequence of thr Operon Irrepressible by Isoleucine and Resistance of thr Operon to Isoleucine Mutation-induced pTHR(*) vectors were recovered using a conventional method from the 27 candidate strains obtained in Example 3 and then a threonine-producing strain, *E. coli* KCCM 10236 was transformed with the pTHR(*) vectors. The recombinant *E. coli* KCCM 10236 strains were plated onto LB media containing 50 mg/l of kanamycin to obtain colonies grown on the LB media. The obtained recombinant strains containing the pTHR(*) vectors, total 135 strains were cultured on solid media of Table 3. Then, one loopful of each culture was inoculated in a flask containing the fermentation medium of Table 4 and cultured for 48 hours. The accumulated amount of L-threonine was analyzed. According to the analysis results, two types of the pTHR(*)-containing strains produced threonine at increased levels of 14% and 22%, respectively, when compared to the parent strain, *E. coli* KCCM 10236. In particular, the pTHR(*) vector obtained from the latter strain was designated as pTHR(+) vector. After the pTHR(+) vector was inserted into *E. coli* w3110 (ATCC27325), the obtained strain was designated as *E. coli* w3110/pTHR(+) and then deposited in the Korean Federation of Culture Collection (KFCC) on Apr. 16, 2002 (accession number: KCCM-10371).

In order to determine the resistance of the recombinant strain, *E. coli* KCCM 10236(pTHR) to L-isoleucine, the productivity of threonine was examined in varying concentration of L-isoleucine-containing media. The results are shown in Table 5.

TABLE 3

Solid medium for threonine production

| Composition | Concentration |
|---|---|
| Glucose | 2% |
| Magnesium sulfate | 2 mM |
| Calcium chloride | 0.1 mM |
| Disodium hydrogenphosphate | 6 g/L |
| Sodium chloride | 0.5 g/L |
| Ammonium chloride | 1 g/L |
| Potassium dihydrogenphosphate | 3 g/L |
| L-methionine | 0.1 g/L |
| L-isoleucine | 0.1 g/L |
| Yeast extract | 10 g/L |
| Agar | 18 g/L |
| pH 7.2 | |

TABLE 4

Liquid medium for threonine production

| Composition | Concentration |
|---|---|
| Glucose | 50 g/L |
| Yeast extract | 2 g/L |
| Ammonium sulfate | 17 g/L |
| Magnesium sulfate | 1 g/L |
| Sodium chloride | 1 g/L |
| Ferrous sulfate | 0.01 g/L |
| Manganese sulfate | 0.01 g/L |
| L-methionine | 0.7 g/L |
| Trace element | 1 ml/L |
| L-isoleucine | 50 mg/L or 200 mg/L |
| Calcium carbonate | 30 g/L |
| Potassium dihydrogenphosphate | 0.3 g/L |
| Potassium phsphate, dibasic | 0.6 g/L |

TABLE 5

Effect of concentration of L-isoleucine on productivity of L-threonine in *E. coli* KCCM 10236 containing pTHR(+)

| amount of L-isoleucine (g/l) | Concentration of L-threonine (g/l) | Productivity of L-threonine (%) |
|---|---|---|
| 0 | 20.2 | 40.4 |
| 0.05 | 18.2 | 36.4 |
| 0.10 | 17.2 | 34.4 |
| 0.20 | 17.5 | 35.0 |
| 0.40 | 16.5 | 33.0 |

As shown in Tables 2 and 5, in the case of the *E. coli* KCCM 10236/pTHR(+), reduction rate of the productivity of L-threonine depend on increase of the concentration of L-isoleucine was considerably decreased, when compared to the parent strain, *E. coli* KCCM 10236. Therefore, It can be seen that the pTHR(+) vector contains the mutated thr operon for L-threonine biosynthesis that is not repressible by L-isoleucine.

Example 5

Identification of Mutation Site

In order to identify mutation site in the thr operon as obtained in Example 4, the nucleotide sequence of the thr operon within the pTHR(+) vector was analyzed. For this, PCR was carried out using 0.1 mg of pTHR(+) as a template, 2 mM of thr-F (SEQ ID NO: 3) as a primer, and 1 μl of BigDye™ Terminator Cycle Sequencing v2.0 Ready Reaction (PE Biosystems). PCR conditions were as follows: denaturation at 95° C. for 30 seconds, annealing at 56° C. for 30 seconds, and amplification at 72° C. for 30 seconds. After 30 cycles, the PCR reaction was terminated at 4° C. The amplified nucleotide sequence was determined using ABI PRISM 3100 Genetic Analyzer (Applied Biosystems). According to the analysis result, it was found that a 39 bp nucleotide sequence of −56 to −18 that maps before the structural thr operon was deleted. The nucleotide sequence of the obtained thr operon is as set forth in SEQ ID NO:2.

The productivity of threonine in the obtained thr operon was investigated. For this, three types of strains, *E. coli* KCCM 10236, *E. coli* KCCM 10236/pTHR(+), and *E. coli* KCCM 10236/pECCG were cultured in flasks containing media for threonine production. The productivities of threonine in the strains were evaluated.

In detail, the three strains were cultured overnight in 32° C. incubator containing the media for threonine production of Table 3. One loopful of each of the obtained single colonies was inoculated on 25 ml of the medium of Table 4 and cultured for 48 hours at 32° C. and 250 rpm. The concentration of the produced L-threonine was measured with High Performance Liquid Chromatography (HPLC). The results are presented in Table 6.

TABLE 6

Comparison of threonine production between a parent strain and a selected recombinant strain in a flask

| Concentration of isoleucine (mg/L) | Strain | Concentration of threonine (g/L) |
|---|---|---|
| 50 | E. coli KCCM 10236 (parent strain) | 16.9 |
|  |  | 16.2 |
|  |  | 16.5 |
|  | E. coli KCCM 10236/pECCG | 16.8 |
|  |  | 16.2 |
|  |  | 16.5 |
|  | E. coli KCCM 10236/pTHR(+) | 19.8 |
|  |  | 20.2 |
|  |  | 20.5 |
| 200 | E. coli KCCM 10236 (parent strain) | 8.76 |
|  |  | 8.39 |
|  |  | 9.48 |
|  | E. coli KCCM 10236/pECCG | 8.15 |
|  |  | 9.06 |
|  |  | 9.24 |
|  | E. coli KCCM 10236/pTHR(+) | 16.1 |
|  |  | 16.3 |
|  |  | 16.6 |

As shown in Table 6, the productivity of threonine in the recombinant strain, E. coli KCCM 10236/pTHR(+) was enhanced by 22%, when compared to the parent strain, E. coli KCCM 10236. In the presence of isoleucine at high concentration (200 mg/l), the productivity of threonine in the parent strain, E. coli KCCM 10236 was reduced by 46%. On the other hand, the productivity of threonine in the E. coli KCCM 10236/pTHR(+) was reduced only by 18.9%. Therefore, it can be seen that the strains containing the thr operon of the present invention have an increased resistance to isoleucine repression.

INDUSTRIAL APPLICABILITY

As apparent from the above description, the present invention provides a nucleotide sequence of the thr operon of E. coli with a deletion of all or part of a 39 bp nucleotide fragment of −56 to −18 that is attenuator of the structural genes of the thr operon. In addition, a recombinant vector containing the nucleotide sequence of the thr operon and a transformed host cell containing the recombinant vector are provided.

Therefore, the transformed host cell of the present invention can produce L-threonine in large scale even in the presence of isoleucine.

What is claimed is:

1. A nucleotide sequence of the threonine operon of *E. coli* with a deletion of 39 bp (−56 to −18) of an attenuator as set forth in SEQ ID NO:2.

2. A recombinant vector containing the nucleotide sequence according to claim 1.

3. The recombinant vector according to claim 2, wherein a cloning vector for the recombinant vector is pECCG122 obtained from KFCC 10696.

4. The recombinant vector according to claim 2, which is pTKR(+).

5. A transformed host cell containing the recombinant vector according to claim 2, wherein the host cell is maintained in vitro.

6. The transformed host cell according to claim 5, wherein the host cell is *Escherichia* sp. or *Corynebacteria* sp.

7. The transformed host cell according to claim 5, wherein the host cell is *E.coli* KCCM 10236.

8. A method for producing L-threonine comprising:

culturing the transformed host cell according to claim 5; and recovering L-threonine from the culture.

* * * * *